US006391034B1

(12) United States Patent
Adamson et al.

(10) Patent No.: US 6,391,034 B1
(45) Date of Patent: May 21, 2002

(54) SURGICAL DEVICE AND METHOD FOR REMOVING UNWANTED TISSUE

(75) Inventors: Christopher D. Adamson, Tampa; Darrel M. Adamson; Brandon M. Adamson, both of Sarasota, all of FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/638,688

(22) Filed: Aug. 15, 2000

(51) Int. Cl.[7] .............................. A61B 17/50
(52) U.S. Cl. ..................................... 606/131
(58) Field of Search ............... 606/131, 172, 606/180; 600/569, 562; 451/177, 178

(56) References Cited

U.S. PATENT DOCUMENTS

| | | | | |
|---|---|---|---|---|
| 2,867,214 A | * | 1/1959 | Wilson | |
| 2,881,763 A | * | 4/1959 | Robbins | |
| 2,921,585 A | * | 1/1960 | Schumann | |
| 3,468,079 A | * | 9/1969 | Kaufman | |
| 3,608,553 A | * | 9/1971 | Balamuth | |
| 4,378,804 A | * | 4/1983 | Cortese, Jr. | |
| 4,572,187 A | * | 2/1986 | Schetrumpf | |
| 5,873,881 A | * | 2/1999 | McEwen et al. | 606/131 X |

FOREIGN PATENT DOCUMENTS

JP          11-225601         *   8/1999

* cited by examiner

Primary Examiner—Jeffrey A. Smith
(74) Attorney, Agent, or Firm—Howard & Howard

(57) ABSTRACT

A surgical device (10) for removing unwanted tissue is disclosed. The surgical device (10) includes a housing (12) having a cavity (14) with a lateral opening. The ends of the cavity (14) are enclosed by an endplate (20) and at a distal end by a motor mount (24). The motor mount (24) provides for the mounting of a pneumatic motor (42). The pneumatic motor (42) drives a cylindrical wire brush (46). The cylindrical wire brush (46) includes a plurality of wire bristles (50) extending radially from a central shaft (48). The pneumatic motor (42) rotatably drives the central shaft (48) at a first end (52) and a high speed bearing (56) mounted in the end plate (20) supports the central shaft (48) at a second end (54). The cylindrical wire brush (46) extends out of the lateral opening (16) in the cavity (14) a predetermined dimension (X). The predetermined dimension may be adjusted with an adjustment mechanism (58) provided to vary the depth of tissue removal. The cavity (14) includes an evacuation chamber (76) that terminates at an evacuation port (38). The evacuation chamber (76) accumulates unwanted tissue that has been removed and provides a conduit through which the waste tissue is removed from the cavity (14). Additionally disclosed is a method of removing unwanted tissue by extending the cylindrical wire brush (46) outside the lateral opening (16) of the cavity (14) the predetermined dimension (X), actuating the cylindrical wire brush (46) within the cavity (14), removing the unwanted tissue with the cylindrical wire brush (46), confining the removed tissue within the cavity (14), and evacuating the removed tissue through the evacuation chamber (76) and evacuation port (38).

21 Claims, 4 Drawing Sheets

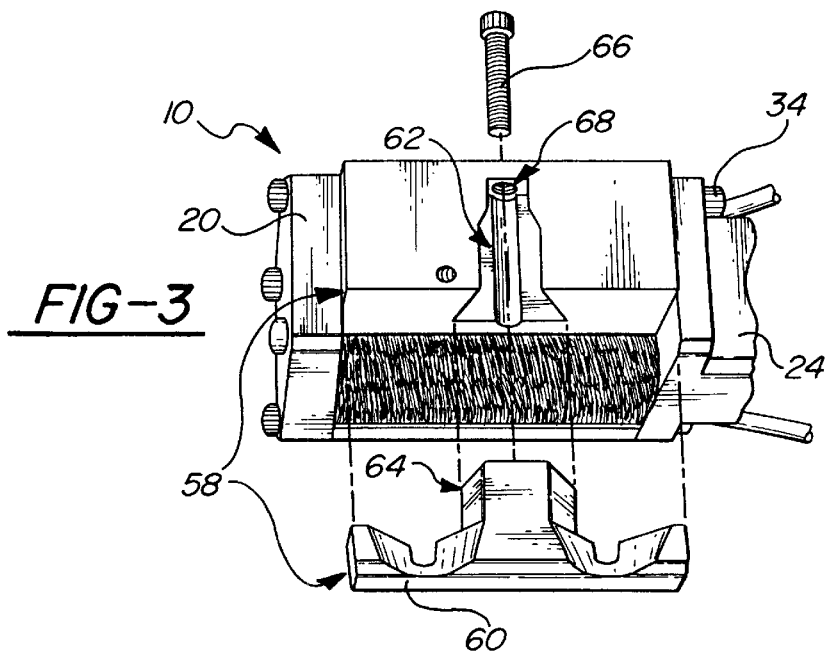
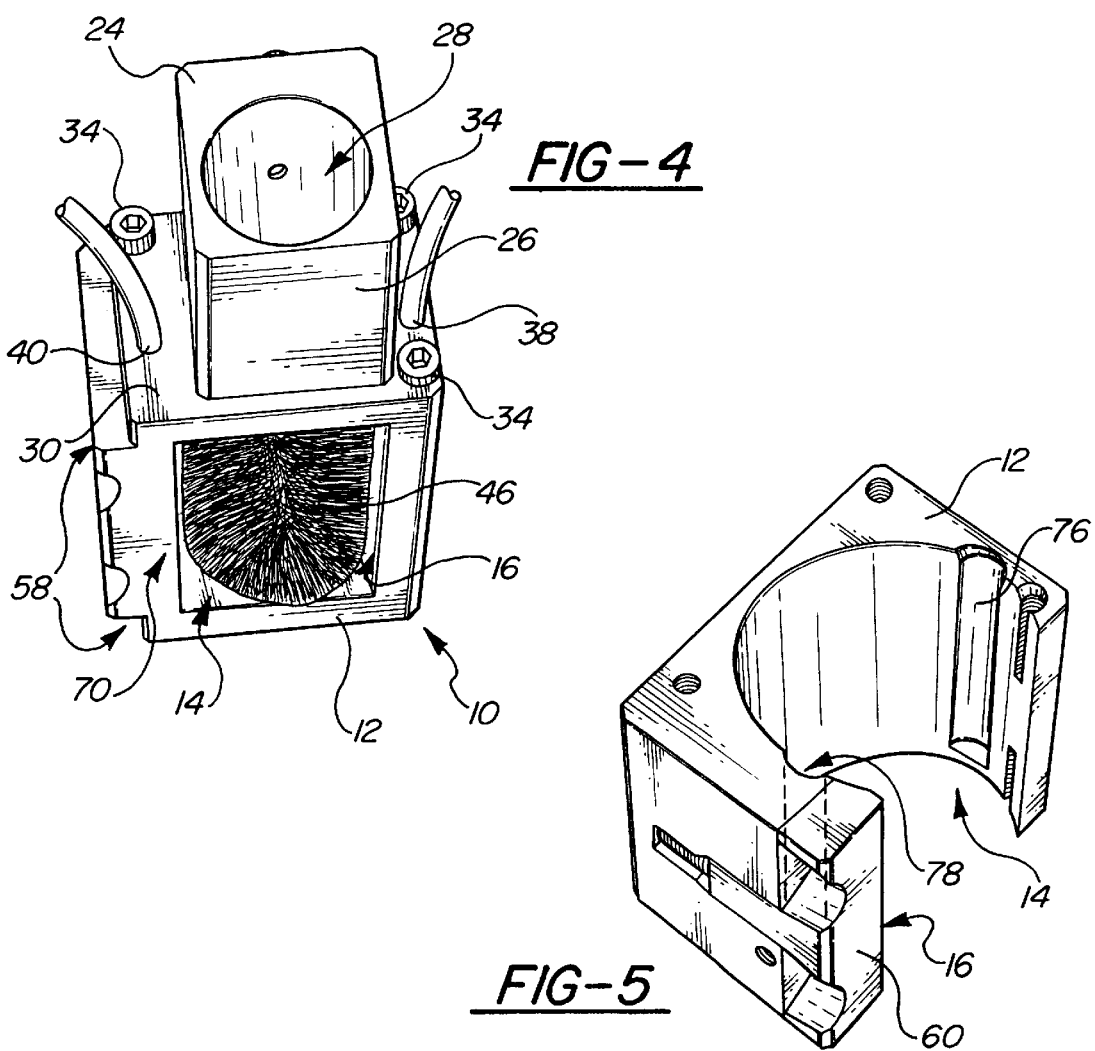

SURGICAL DEVICE AND METHOD FOR REMOVING UNWANTED TISSUE

BACKGROUND OF THE INVENTION

1. Field of the Invention

The subject invention relates to a surgical device and method for removing unwanted tissue.

2. Description of the Prior Art

Serious burn injuries are typically classified by the depth and extent of the burn. Third degree burns are the most serious burn injury, because damage is done to the outer most layer of skin or epidermis, the inner most layer of skin or dermis, and to underlying tissue. A typical treatment for third degree burn damaged tissue includes removing the damaged tissue and transplanting new tissue.

Removal of damaged tissue is typically accomplished by manually cutting away the damaged tissue with specially designed tools such as a Weck scalpel or a Goulian Blade. The damaged tissue is removed to expose the underlying healthy tissue. Performance of this procedure is tedious and time consuming for a surgeon. The length of time complicates the procedure because a patient is typically placed under a general anesthetic. It is desirable to minimize the amount of time a patient is under the general anesthetic. Another complication arises because the depth with which the damaged tissue is removed cannot be controlled precisely, such that inevitably healthy tissue is also removed.

A dermabrasion device has been used to reduce the amount of time required for removing damaged tissue. A typical dermabrasion device is disclosed in the U.S. Pat. No. 4,572,187 to Schetrumpf. The abrasion device includes a rotary hub and a plurality of flexible strips. Each strip has a single abrasive surface. The strips project radially from the rotary hub. The rotary hub includes a shaft that is rotated by a drive. In operation the abrasion device is rotated by the drive and the flexible stripes are placed in contact with the damaged tissue to be removed. Using the abrasion device minimizes the time required to remove unwanted and damaged tissue. However, the abrasion device is not precise, i.e., more tissue is removed because of lack of control over the depth of penetration. Because of the imprecise nature of the abrasion device, healthy tissue will inevitably be removed. Also, abraded away waste tissue is spread and splattered about the operating room during the procedure, creating health and safety concerns.

The prior art devices include some inherent deficiencies that demonstrate a need for a device that quickly removes unwanted tissue, precisely controls the depth of tissue removal, and controls the evacuation of removed tissue from the burn damaged area.

SUMMARY OF THE INVENTION AND ADVANTAGES

The invention provides a surgical device to remove unwanted tissue including a housing having a cavity with a lateral opening, a member for removing unwanted tissue supported by the housing and extending out of the opening a predetermined dimension, and a drive for actuating the element. The surgical device is characterized by an evacuation chamber within the cavity and terminating at an evacuation port. The surgical device is further characterized by an adjustment mechanism for adjusting the predetermined dimension to vary the depth of tissue removal.

The invention also includes a method of removing tissue utilizing a device having a member for removing unwanted tissue supported within a housing, actuated by a drive and disposed within a cavity having a lateral opening and an evacuation chamber, the method includes the steps of extending the member for removing unwanted tissue outside the lateral opening a predetermined dimension, actuating the member for removing tissue within the cavity, and removing the unwanted tissue. The method is characterized by confining the removed tissue within the cavity and evacuating the removed tissue through the evacuation chamber.

Accordingly, the invention provides a surgical device and method for removing unwanted tissue quickly so as to minimize the time a patient must spend under general anesthetic. Further, the invention provides for the adjustment and precise control of the depth of unwanted tissue removed, while controlling the evacuation of removed unwanted tissue.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 3 is a perspective view similar to FIG. 1 showing the adjustment mechanism exploded;

FIG. 4 is a perspective view of the motor mount of the surgical device illustrating the irrigation and evacuation ports;

FIG. 5 is a perspective view of the cavity of the surgical device;

DETAILED DESCRIPTION OF THE PREFERRED EMBODIMENT

Figure 1:
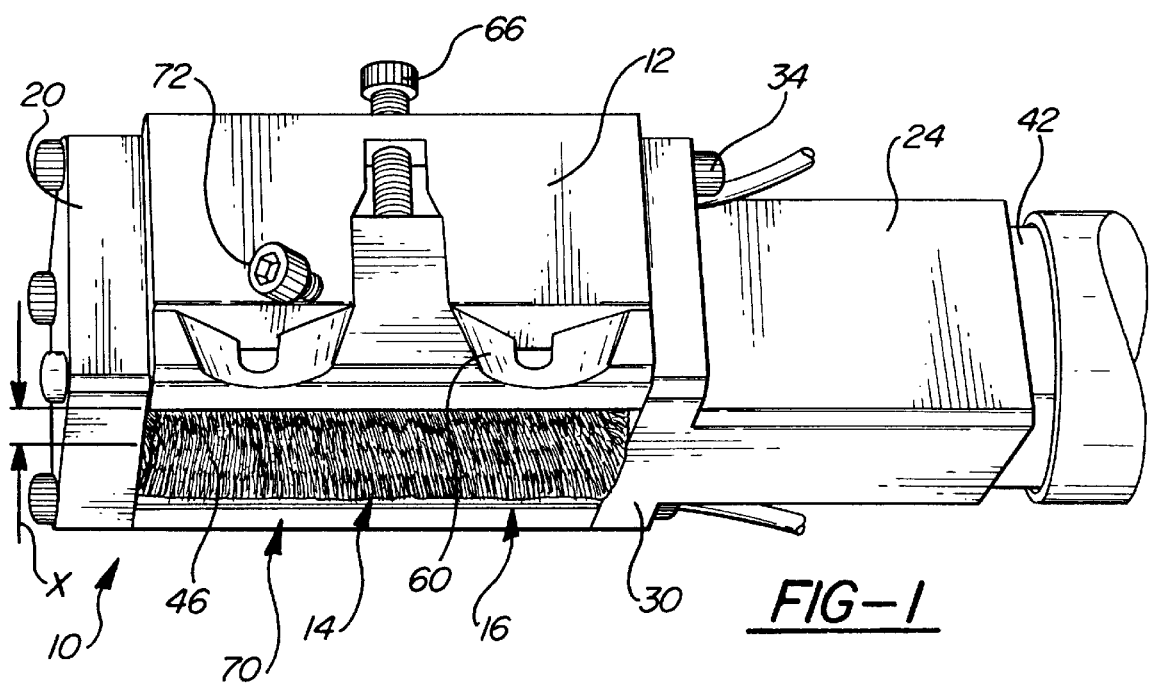
FIG. 1 is a perspective view of the front of a surgical device for removing unwanted tissue.
Figure 2:
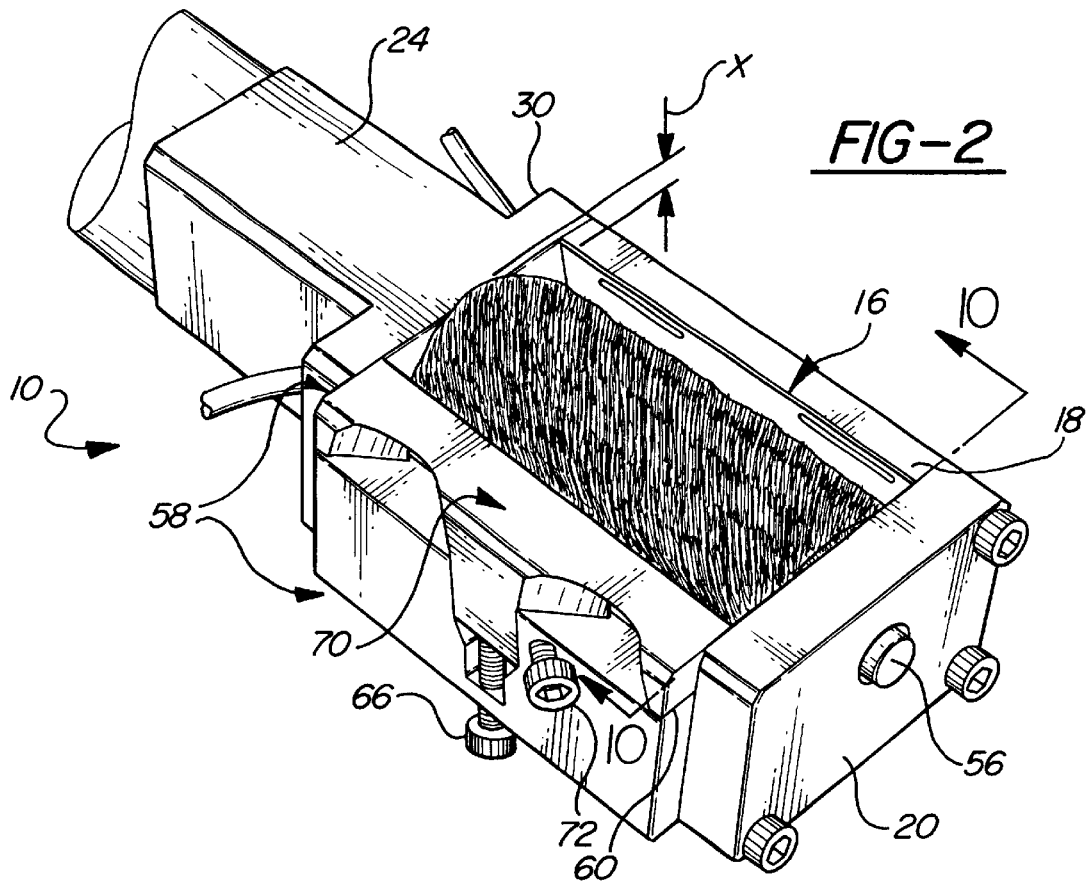
FIG. 2 is a perspective view of the bottom of the surgical device.

A surgical device is generally shown at 10 in FIGS. 1,2,3 and 10 for removing unwanted tissue. The surgical device 10 includes a housing 12 having a cavity 14 with a lateral opening 16. The cavity 14 is generally a semi-circle bored through a width of the housing 12. The cavity 14 opens at a bottom side of the housing 12. The ends of the cavity 14 are enclosed at a first end 18 by an endplate 20 and at a second end 22 by a motor mount 24.

Referring to FIG. 4, the motor mount 24 includes a generally rectangular body 26 with an opening 28. The rectangular body 26 is fixed to a mounting flange 30. The mounting flange 30 includes at least two mounting holes 32 for at least two mounting bolts 34 having external threads. The motor mount 24 is attached to the housing 12 by the bolts 34. The bolts 34 extend through the mounting holes 32 in the mounting flange 30 and engage correspondingly threaded mounting holes 36 in the housing 12. The mounting flange 30 also includes an evacuation port 38 and an irrigation port 40. The motor mount 24 provides for the mounting of a drive.

The drive is comprises a pneumatic motor 42 secured within the opening 28 in the body 26 of the motor mount 24. Specifically shown is a hexagonal high-speed pneumatic motor 42 secured within the body 26 of the motor mount 24 by a pair of threaded bolts (not shown). The threaded bolts thread into a pair of correspondingly threaded holes (not shown) in the body of the motor mount and extend into the opening contacting and applying a holding pressure to the pneumatic motor 42. The pneumatic motor 42 is provided air through an air hose 44. As appreciated the air hose 44 is connected to a source of air (not shown).

Figure 6:
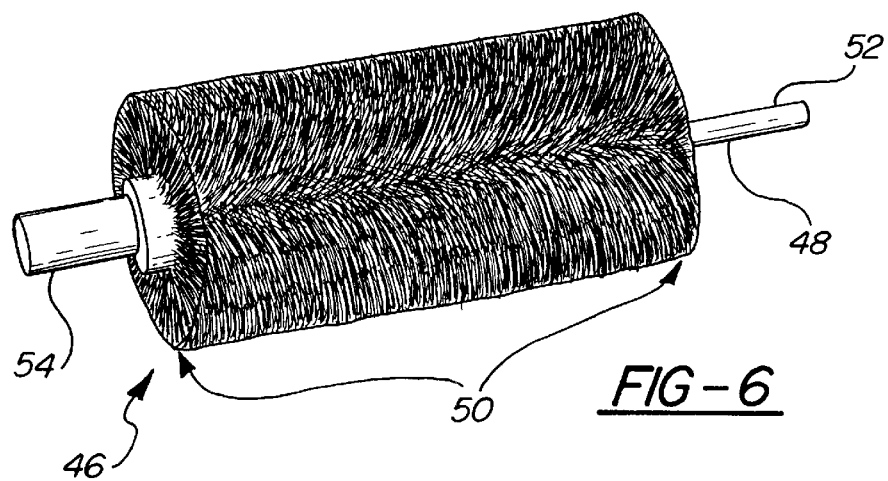
FIG. 6 is a perspective view of the wire brush embodiment of the member for removing unwanted tissue.

The pneumatic motor 42 drives a member comprising a wire brush 46 for removing unwanted tissue. Referring to FIG. 6, preferably the wire brush 46 is a cylinder and extends axially along a center axis. The wire brush 46 includes a central shaft 48 driven by the pneumatic motor 42. The cylindrical wire brush 46 includes a plurality of wire bristles 50 extending radially from the central shaft 48. The pneumatic motor 42 is drivingly attached to the central shaft 48 at a first end 52. A high-speed bearing 56 mounted in the end plate 20 supports a second end 54 of the central shaft 48. The high-speed bearing 56 may be of any type known in the art.

Referring back to FIGS. 1 and 2, the cylindrical wire brush 46 extends radially out of the lateral opening 16 in the cavity 14 a predetermined dimension X. Referring to FIG. 3, the predetermined dimension X may be adjusted with an adjustment mechanism 60 provided to vary the depth of tissue removal. The adjustment mechanism includes an adjustment bracket 60 slidingly attached to the housing 12. The attachment of the adjusting bracket 60 to the housing 12 is accomplished by providing a mortised groove 62 in the housing 12 and a corresponding tenon 64 in the adjustment bracket 60. The tenon 64 of the adjustment bracket 60 slidingly engages the mortised groove 62. A threaded adjusting screw 66 extends through a threaded hole 68 in the housing 12 and contacts the adjustment bracket 60. By threading the adjustment screw 66 either into or out of the housing 12 and then butting the adjustment bracket 60 against an end of the adjusting bolt 66, the predetermined dimension X that the cylindrical wire brush 46 extends above the lateral cavity 14 can be precisely set. As appreciated, this is accomplished by either raising or lowering the adjustment bracket 60 that effectively raises or lowers a lip 70 of the lateral cavity 14 relative to the cylindrical wire brush 46. The adjustment mechanism 58 also includes an externally threaded set screw 72 that is threaded into a correspondingly threaded hole 74 in the housing 12. Once the desired predetermined dimension X is set, the set screw 72 is threaded through the housing 12 and against the tenon 64 of the adjustment bracket 60 to lock the adjustment bracket 60 in place thereby locking in the predetermined dimension X to precisely set the depth of tissue removal.

Referring to FIG. 5, the surgical device 10 is characterized by an evacuation chamber 76 within the cavity 14 and terminating at the evacuation port 38. The evacuation chamber 76 acts to accumulate unwanted tissue that has been removed and to provide a conduit with which the waste tissue is removed from the cavity 14. Preferably the evacuation chamber 76 is a lateral groove within the cavity 14 and extending the length of the cavity 14. The evacuation chamber 76 terminates at the evacuation port 38 disposed within the mounting flange 30. The evacuation port 38 provides for connection to an external vacuum source (not shown). Preferably the connection will include a quick disconnect fitting (not shown) as known in the art. As appreciated, a quick disconnect fitting provides for convenient and easy connection to the external vacuum source without the use of additional tools.

The cavity 14 further includes an irrigation chamber 78. Preferably, the irrigation chamber 78 is a laterally extending groove disposed within the cavity 14 and opposite the evacuation chamber 76. The irrigation chamber 78 terminates at the irrigation port 40 disposed in the mounting flange 30 of the motor mount 24. Irrigation fluid from an external source is passed through the irrigation port 40 and into the irrigation chamber 78 to be injected into the cavity 14. As appreciated irrigation of a wound aids in the effective removal of unwanted tissue.

Figure 7:
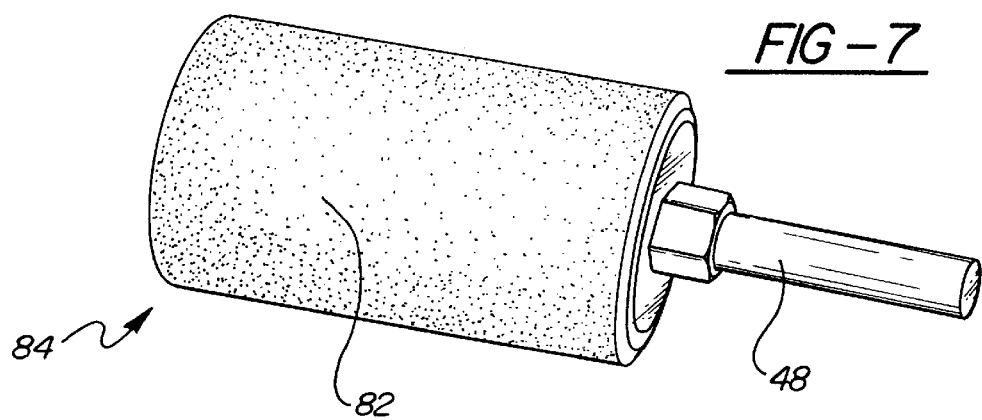
FIG. 7 is a perspective view of the abrasive cylinder embodiment of the member for removing unwanted tissue.
Figure 8:
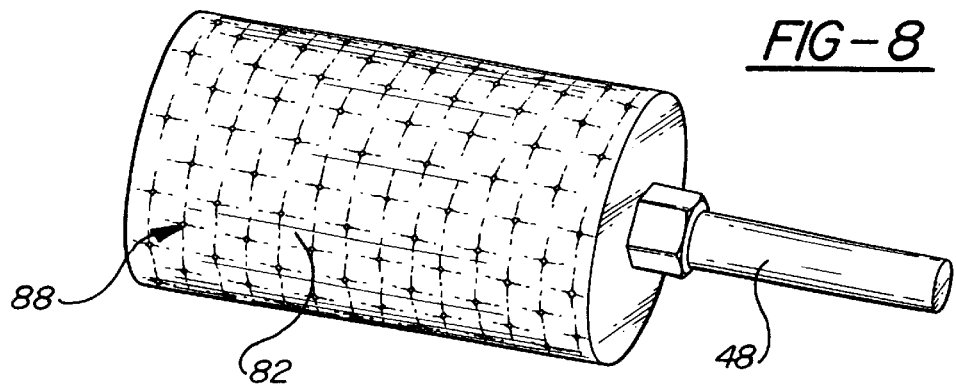
FIG. 8 is a perspective view of the cutting holes cylinder embodiment of the member for removing unwanted tissue.
Figure 9:
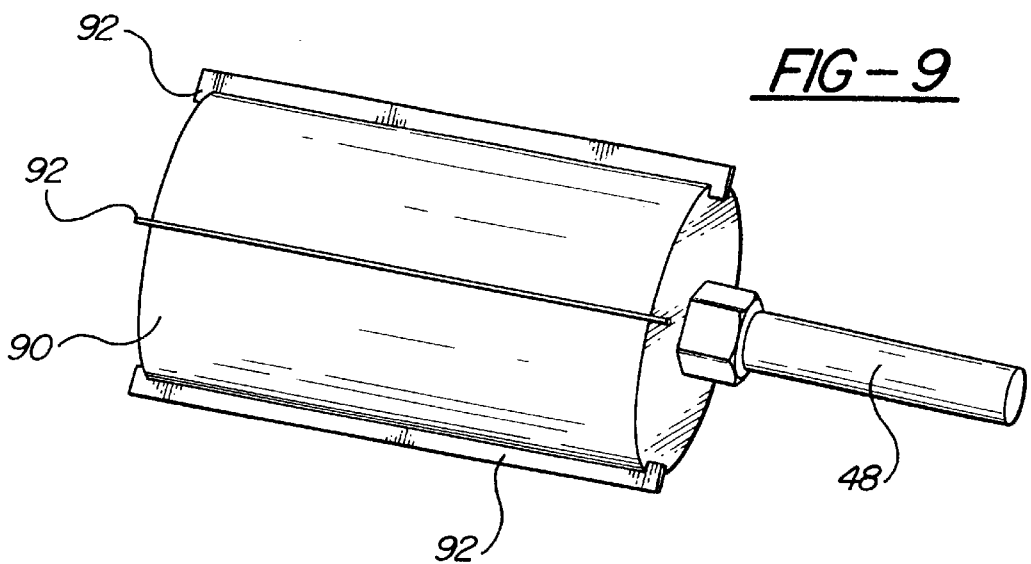
FIG. 9 is a perspective view of the cutting blade embodiment of the member for removing unwanted tissue.

It is within the contemplation of this invention that the member for removing unwanted tissue may be of any configuration known in the art. Specifically, referring to FIG. 7, the member for removing unwanted tissue is further defined as an abrasive cylinder 80 having an abrasive surface 82 concentrically supported about the central shaft 48. The abrasive surface 82 of the abrasive cylinder 80 may comprise any abrasive known in the art including carbide and diamond. Further, the member for removing unwanted tissue may include a cutting surface instead of an abrasive surface or wire brush. Referring to FIG. 8, the member for removing unwanted tissue is an cutting cylinder 84 including a surface 86 having a plurality of cutting holes 88 concentrically positioned about the central shaft 48. The plurality of cutting holes 88 disposed about the surface 86 of the cylinder 84 cuts away unwanted tissue. Referring to FIG. 9, another embodiment of a cutting surface is disclosed. The member for removing unwanted tissue is a mounting cylinder 90 supporting a plurality of lateral blades 92 projecting radially outward and concentrically supported about the central shaft 48.

Figure 10:
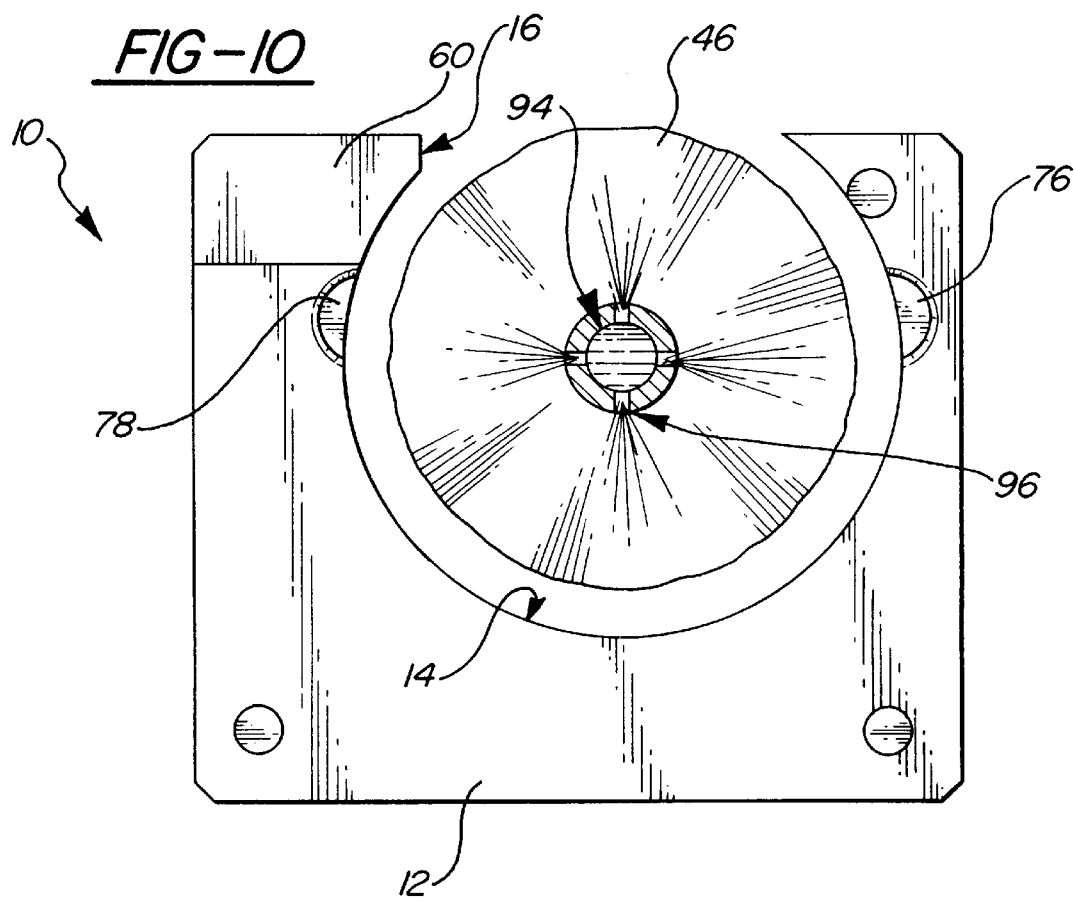
FIG. 10 is a cross sectional view taken along line 10—10 of FIG. 2 shown a hollow central shaft embodiment for irrigating the cavity.

An additional embodiment discloses an alternate means for irrigating the tissue removal area. Referring to FIG. 10, a hollow central shaft 94 with a plurality of holes 96 disposed along the central shaft length. Irrigation fluid pumped from an external source is passed through the hollow central shaft 94 and injected through the plurality of holes 96 into the cavity 14. This configuration allows for direct irrigation of the tissue removal area evenly along the member for removing unwanted tissue. Preferably the hollow central shaft 94 configuration would by utilized with the cylindrical wire brush 46. As appreciated, any configuration of the member to remove unwanted tissue may be adapted for direct irrigation by use of the hollow central shaft 94.

The subject invention also provides a method of removing unwanted tissue utilizing a surgical device having a member 46, 80, 84, and 90 for removing unwanted tissue supported within a housing 12, actuated by a drive 42 and disposed within a cavity 14 having a lateral opening 16 and an evacuation chamber 76. The method includes the steps of extending the member 46, 80, 84, and 90 for removing unwanted tissue outside the lateral opening 16 a predetermined dimension X. The step of extending the member 46, 80, 84, and 90 for removing unwanted tissue outside the lateral opening 16 includes the step of adjusting the predetermined dimension X of the member for removing tissue outside the lateral opening 16. As appreciated, adjusting the predetermined dimension X provides for varying the depth of tissue removal. The method continues by actuating the member 46, 80, 84, and 90 for removing tissue within the cavity 14 and removing the unwanted tissue with the actuating member 46, 80, 84, and 90 for removing unwanted tissue.

The method is characterized by confining removed tissue within the cavity 14 and evacuating the removed tissue through the evacuation chamber 76. The method further includes the step of irrigating the cavity 14 and the member 46, 80, 84, and 90 for removing tissue during the removal of tissue. Irrigating the cavity 14 can be further defined by irrigating the cavity 14 through the member 46, 80, 84, and 90 for removing tissue.

Obviously, many modifications and variations of the present invention are possible in light of the above teachings. The invention may be practiced otherwise than as specifically described within the scope of the appended claims, wherein that which is prior art is antecedent to the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the incentive novelty exercises its utility. In addition, the reference numerals in the claims are merely for convenience and are not to be read in any way as limiting.

What is claimed is:

1. A surgical device (10) to remove unwanted tissue comprising:

a housing (12) having a cavity (14) with a lateral opening (16);

a rotating member for removing unwanted tissue and rotatably supported by said housing (12) and extending out of said opening a predetermined dimension (X) for removing unwanted tissue as the housing (12) is moved over tissue;

a drive (42) for rotating said member for removing the unwanted tissue;

said surgical device (10) characterized by an evacuation chamber (76) opening into said cavity (14) and terminating at an evacuation port (30) for collecting the unwanted tissue as it is removed by the rotating members and transferring the unwanted tissue out the evacuation port (30) to a remote location, and an adjustment mechanism (58) for adjusting said predetermined dimension (X) to vary the depth of tissue removal.

2. A surgical device (10) as set forth in claim 1 were said adjustment mechanism (58) comprises an adjustment bracket (60) slidingly attached to said housing (12).

3. A surgical device (10) as set forth in claim 2 were said adjustment mechanism (58) comprises a mortised groove (62) in said housing (12) and said adjustment bracket (60) having a tenon (64) to slidingly engage said mortised groove (62) and an adjusting screw (66) extending through a threaded hole (68) in said housing (12) and contacting said adjustment bracket (60), and a set screw (72) threaded through said housing (12) and contacting said adjusting bracket (60) at said tenon (64) to lock the adjustment bracket (60) in place.

4. The device as set forth in claim 1 were said evacuation chamber (76) is a lateral groove within said cavity (14).

5. The device as set forth in claim 4 were said cavity (14) includes an irrigation chamber (78), said irrigation chamber (78) terminates at an irrigation port (40) through which irrigation fluid is injected into said cavity (14).

6. The device as set forth in claim 5 including a motor mount (24) attached to said housing (12) for securing said drive (42), said motor mount (24) comprises a body (26) having an opening (28) fixed to a mounting flange (30), said mounting flange (30) includes said evacuation port (38) and said irrigation port (40).

7. The device as set forth in claim 6 were said drive (42) is a pneumatic motor mounted in said opening (28) of said motor mount body (26).

8. The device as set forth in claim 7 were said member for removing unwanted tissue includes a central shaft (48) connected to said pneumatic motor (42), whereby said pneumatic motor (42) rotates said central shaft (48).

9. The device as set forth in claim 8 were said central shaft (48) is hollow with a plurality of holes (96) disposed along a length of said central shaft (48), whereby irrigation fluid is passed through said central shaft (48) and injected through said plurality of holes (96) into said cavity (14).

10. The device as set forth in claim 8 were said member for removing unwanted tissue is further defined as a cylindrical wire brush (46) comprising a plurality of wire bristles (50) extending radially from said central shaft (48).

11. The device as set forth in claim 8 were said member for removing unwanted tissue is further defined as an abrasive cylinder (80) having an abrasive surface (82) concentrically supported about said central shaft (48).

12. The device as set forth in claim 11 were said abrasive surface (82) comprises carbide.

13. The device as set forth in claim 11 were said abrasive surface (82) comprises diamond.

14. The device as set forth in claim 8 were said member for removing unwanted tissue is a cutting cylinder (84) including a surface (86) having a plurality of cutting holes (88) concentrically positioned about said central shaft (48).

15. The device as set forth in claim 8 were said member for removing unwanted tissue is a mounting cylinder (90) supporting a plurality of lateral blades (92) projecting radially outward and concentrically supported about said central shaft (48).

16. A surgical device (10) to remove unwanted tissue comprising:

a housing (12) having a cavity (14) with a lateral opening (16);

a member for removing unwanted tissue supported by said housing (12) and extending out of said opening a predetermined dimension (X);

a drive (42) for actuating said member for removing unwanted tissue;

said surgical device (10) characterized by an adjustment bracket (60) slidingly attached to said housing (12) for adjusting said predetermined dimension (X) to vary the depth of tissue removal.

17. A surgical device (10) as set forth in claim 16 were said adjustment mechanism (58) comprises a mortised groove (62) in said housing (12) and said adjustment bracket (60) having a tenon (64) to slidingly engage said mortised groove (62) and an adjusting screw (66) extending through a threaded hole (68) in said housing (12) and contacting said adjustment bracket (60), and a set screw (72) threaded through said housing (12) and contacting said adjusting bracket (60) at said tenon (64) to lock the adjustment bracket (60) in place.

18. A method of removing unwanted tissue utilizing a device having a rotating member for removing unwanted tissue supported within a housing (12), rotated by a drive (42) and disposed within a cavity (14) having a lateral opening (16) and an evacuation chamber (76) opening into the cavity (14), said method comprising the steps of:

extending the rotating member (46, 80, 84, 90) for removing unwanted tissue outside the lateral opening (16) a predetermined dimension (X);

rotating the member (46, 80, 84, 90) for removing the unwanted tissue and moving the unwanted tissue into the cavity (14);

said method is characterized by confining the removed tissue within the cavity (14) and evacuating the removed tissue through the evacuation chamber (76).

19. A method as set forth in claim 18 further including the step of adjusting the predetermined dimension (X) of the member (46, 80, 84, 90) for removing tissue outside the lateral opening (16), thereby varying tissue removal depth.

20. A method as set forth in claim 19 further defined by irrigating the cavity (14) and the member (46, 80, 84, 90) for removing tissue during said removing of tissue.

21. A method as set forth in claim 20 further defined by irrigating the cavity (14) through the member (46, 80, 84, 90) for removing tissue.

\* \* \* \* \*